US00PP25069P3

(12) United States Plant Patent
Zaiger et al.

(10) Patent No.: US PP25,069 P3
(45) Date of Patent: Nov. 18, 2014

(54) CHERRY TREE NAMED 'ROYAL BELLE'

(50) Latin Name: *Prunus avium*
Varietal Denomination: Royal Belle

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 123 days.

(21) Appl. No.: 13/815,392

(22) Filed: Feb. 28, 2013

(65) Prior Publication Data

US 2014/0245500 P1 Aug. 28, 2014

(51) Int. Cl.
*A01H 5/00* (2006.01)

(52) U.S. Cl.
USPC ..... Plt./181

(58) Field of Classification Search
USPC ..... Plt./181
See application file for complete search history.

*Primary Examiner* — Annette Para

(57) ABSTRACT

A new and distinct variety of cherry tree. The following features of the tree and its fruit are characterized with the tree budded on 'Mahaleb' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Early blooming with a low winter chilling requirement of approximately 550 hours at or below 45° F.
2. Fruit maturing in the early season.
3. Fruit with attractive red skin color.
4. Regular and productive bearer of large size fruit.
5. Fruit with good flavor and eating quality.

1 Drawing Sheet

Botanical designation: *Prunus avium.*
Variety denomination: 'Royal Belle'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of cherry tree was originated and asexually reproduced by us in our experimental orchard located near Modesto, Stanislaus County, Calif.

2. Prior Varieties

Among the existing varieties of cherry trees, which are known to us, and mentioned herein, 'Royal Lee' Cherry (U.S. Plant Pat. No. 12,417), 'Bing' Cherry (non-patented), 'Brooks' Cherry (U.S. Plant Pat. No. 6,676) and our proprietary non-patented cherry seedling selections '20ZD807', '26MA629', '6GK67' and '21ZA1072'.

STATEMENT REGARDING FEDERALLY SPONSORED RESEARCH AND DEVELOPMENT

Not applicable.

ORIGIN OF THE VARIETY

The present new variety of cherry tree (*Prunus avium*) was originated by us in our experimental orchard located near Modesto, Calif. as a first generation cross between our selected proprietary non-patented cherry seedlings '20ZD807' and '26MA629'. The seed parent (20ZD807) cherry (non-patented) originated as a first generation cross between an open pollinated seedling of 'Bing' Cherry (non-patented) and 'Royal Lee' Cherry (U.S. Plant Pat. No. 12,417). The pollen parent (26MA629) cherry (non-patented) originated as a first generation cross between our proprietary non-patented cherry seedling selections '6GK67' and '21ZA1072'. A large group of these first generation crosses were budded on older trees of 'Mahaleb' Rootstock (non-patented) to accelerate earlier fruit production for evaluation. Under close and careful observation the present seedling exhibited desirable fruit and tree characteristics and was selected in 2009 for asexual propagations and commercialization.

ASEXUAL REPRODUCTION OF THE VARIETY

Asexual reproduction of the new and distinct variety of cherry tree was by budding to 'Mahaleb' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of cherry tree is of large size, vigorous, upright growth with a low winter chilling requirement of approximately 550 hours at or below 45° F. The tree is a regular and productive bearer of large size fruit that ripens in the early maturity season. The fruit is further characterized by having an attractive red skin color, good flavor and eating quality. In comparison to its immediate seed parent (20ZD807) cherry (non-patented) the fruit of the new variety ripens approximately 7 days earlier. In comparison to the pollen parent (26MA629) cherry (non-patented) the tree blooms approximately 10 days earlier and the fruit ripens approximately 17 days earlier. In comparison to the commercial variety 'Brooks' Cherry (U.S. Plant Pat. No. 6,676) the fruit of the new variety ripens approximately 20 days earlier.

DESCRIPTION OF THE PHOTOGRAPH

The accompanying color photographic illustration shows typical specimens of the foliage and fruit of the present new cherry variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of cherry tree, its flowers, foliage and fruit, as based on observations of 6 year old specimens grown near Modesto, Calif., with color in accordance with Munsell Book of Color published in 1958.

Tree:

*Size.*—Large. Pruned to 3.0 to 3.5 meters in height and width for economical harvesting of fruit, varies with different cultural practices.

*Vigor.*—Vigorous, tree growth of 1.5 to 2.0 meters in height the first growing season. Growth rate will vary with types of soil, fertility and cultural practices.

*Form.*—Upright, usually pruned to vase shape.

*Branching habit.*—Upright. Crotch angle approximately 45°, increases with heavy crop load.

*Productivity.*—Productive, produces heavy crop annually. Similar in production to the commercial variety 'Brooks' Cherry (U.S. Plant Pat. No. 6,676).

*Bearer.*—Regular, heavy fruit set 4 consecutive years. Set varies with climatic conditions at bloom time. No alternate bearing observed.

*Fertility.*—Self-sterile, pollinator required.

*Density.*—Medium dense, usually pruned to vase shape to increase air movement and sunlight to center of tree to enhance fruit color and health of fruit spurs.

*Hardiness.*—Hardy in all stone fruit growing areas of California. Tree grown in USDA Hardiness Zone 9. Winter chilling requirement approximately 550 hours at or below 45° F.

Trunk:

*Size.*—Large. Average circumference 53.3 cm at 30.5 cm above the ground on a 6 year old tree.

*Stocky.*—Medium stocky.

*Texture.*—Medium rough, roughness increases with age.

*Color.*—Varies from 2.5Y 6/2 to 2.5Y 5/2.

Branches:

*Size.*—Medium. Average circumference 15.4. cm at 1.2 meters above the ground.

*Surface texture.*—New growth relatively smooth. Older growth medium rough, roughness increases with age.

*Lenticels.*—Average number 10 in a 25.8 sq cm section. Average length 6.2 mm. Average width 2.8 mm. Color varies from 10YR 6/10 to 10YR 5/8.

*Color.*—New growth varies from 5GY 5/6 to 5GY 5/8. Older growth varies from 7.5YR 2/2 to 10YR 2/2, varies with age of growth.

Leaves:

*Size.*—Large. Average length 139.2 mm. Average width 57.6 mm.

*Form.*—Lanceolate.

*Apex.*—Acuminate.

*Base.*—Cuneate.

*Margin.*—Serrate.

*Thickness.*—Medium.

*Surface texture.*—Upper surface relatively smooth, slight indentation over leaf veins, glabrous. Lower surface relatively smooth except for slight ridges created by midrib and pinnate venation, glabrous.

*Petiole.*—Average length 38.0 mm. Average width 1.7 mm. Longitudinally grooved. Color varies from 7.5R 2/4 to 2.5GY 5/6. Surface — glabrous.

*Glands.*—Shape — reniform. Average length 2.6 mm. Average width 1.5 mm. Number varies from 3 to 5, average number 2. Located primarily on the upper portion of the petiole and the base of leaf blade. Color varies from 5R 3/8 to 7.5R 3/8.

*Stipules.*—Average length 12.5 mm. Margin — pectinate. Color varies from 2.5GY 5/6 to 2.5GY 5/8.

*Color.*—Upper surface varies from 7.5GY 3/4 to 7.5GY 3/6. Lower surface varies from 5GY 5/4 to 7.5GY 4/4. Midvein color varies from 10Y 6/8 to 2.5GY 6/6.

Flower buds:

*Size.*—Medium to large. Average length 18.2 mm. Average diameter 8.7 mm.

*Hardiness.*—Hardy with respect to California winters.

*Form.*—Conical, becoming elongated just before opening.

*Pedicel.*—Average length 11.6 mm. Average width 1.4 mm. Color varies from 5GY 6/8 with 7.5R 3/6.

*Color.*—N 9.5/(white).

*Number of buds per spur.*—Average number 9, varies from 8 to 11.

Flowers:

*Blooming period.*—Date of First Bloom Mar. 5, 2012. Date of petal fall Mar. 15, 2012, varies slightly with climatic conditions.

*Size.*—Large. Average height 22.4 mm. Average diameter 32.9 mm.

*Petals.*—Size — large. Number — normally 5, alternately arranged to sepals. Average length 17.1 mm. Average width 13.7 mm. Form — obovate. Margin — sinuate. Color N 9.5/(white). Both upper and lower surfaces glabrous.

*Sepals.*—Size — large. Number — normally 5, alternately arranged to the petals. Average length 6.7 mm. Average width 4.5 mm. Form — triangular. Margin — entire. Color — upper surface varies from 5GY 6/6 to 7.5GY 5/6. Lower surface varies from 5GY 5/6 to 7.5R 3/6. Both upper and lower surfaces glabrous.

*Stamens.*—Average number per flower 33, varies from 33 to 34. Average filament length 16.7 mm. Filament color N 9.5/(white). Anther color varies from 5Y 8/8 to 5Y 8/10.

*Pollen.*—Self-sterile, pollinator required. Color varies from 2.5Y 7/12 to 5Y 7/12.

*Pistil.*—Normally 1 per flower. Average length 16.5 mm. Stigma height approximately 2.5 mm below anthers. Color varies from 10Y 7/6 to 2.5GY 7/6. Surface — glabrous.

*Fragrance.*—Moderate aroma.

*Color.*—N 9.5/(white).

*Number flowers per flower bud.*—Average 4, varies from 1 to 5.

*Pedicel.*—Average length 12.0 mm. Average width 1.4 mm. Color varies from 2.5GY 5/8 with 7.5R 3/6.

Fruit:

*Maturity when described.*—Firm ripe.

*Date of first picking.*—Apr. 30, 2012.

*Date of last picking.*—May 10, 2012, varies slightly with climatic conditions.

*Size.*—Large. Average diameter axially 25.5 mm. Average transversely in suture plane 26.5 mm. Average weight 9.6 grams, varies slightly with fertility of the soil, amount of thinning and climatic conditions.

*Form.*—Broadly cordate.

*Suture.*—Nearly smooth, extends from base to apex.

*Ventral surface.*—Nearly smooth.

*Apex.*—Slightly retuse.

*Base.*—Retuse.

*Stem cavity.*—Rounded to slightly elongated in suture plane. Average depth 2.3 mm. Average diameter 4.3 mm.

Stem:

*Size.*—Medium to large. Average length 37.3 mm. Average diameter 1.6 mm.

*Color.*—Varies from 5GY 5/6 to 7.5GY 5/6.

Flesh:

*Ripens.*—Slightly earlier at the apex.

*Texture.*—Very firm.

*Fibers.*—Few, small, tender.

*Firmness.*—Very firm, comparable to most commercial varieties.

*Aroma.*—Very slight.

*Amydgalin.*—Undetected.

*Eating quality.*—Good.

*Flavor.*—Good, good balance between acid and sugar.

*Juice.*—Moderate amount, enhances flavor.

*Brix.*—Average Brix 15.2°, varies slightly with amount of fruit per tree and climatic conditions.

*Color.*—Varies from 2.5Y 9/4 to 5R 3/8. Pit cavity color varies from 5R 3/6 to 7.5R 2/4.

Skin:

*Thickness.*—Medium.

*Surface.*—Smooth.

*Bloom.*—Wanting.

*Tendency to crack.*—None during dry weather. Very slight tendency to crack during wet weather, varies with stage of maturity.

*Color.*—Varies from 7.5R 2/6 to 7.5R 2/8.

*Tenacity.*—Tenacious to flesh.

*Astringency.*—Slight to none.

Stone:

*Type.*—Clingstone.

*Size.*—Medium. Average length 10.1 mm. Average width 9.7 mm. Average thickness 7.8 mm.

*Form.*—Ovoid.

*Base.*—Flat.

*Apex.*—Rounded.

*Surface.*—Very slightly pitted throughout. Small ridges run along each side of the suture line from base to apex.

*Sides.*—Varies from equal to unequal with one side extending further from the suture plane.

*Tendency to split.*—None.

*Color.*—Varies from 10YR 7/6 to 10YR 6/6 when dry.

Kernel:

*Size.*—Small to medium. Average length 7.7 mm. Average width 5.5 mm. Average depth 4.2 mm.

*Form.*—Ovate.

*Viability.*—Partially viable, incomplete embryo in some stones.

*Skin color.*—Varies from 5Y 9/4 to 7.5Y 9/4.

Use:

*Dessert.*—Market — local and long distance.

Keeping quality: Good, held firm in cold storage 2 weeks at 38° to 42° F. without internal breakdown of flesh, shriveling or appreciable loss of flavor.

Shipping quality: Good, showed minimal flesh bruising or skin scarring during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of cherry tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of cherry tree, substantially as illustrated and described.

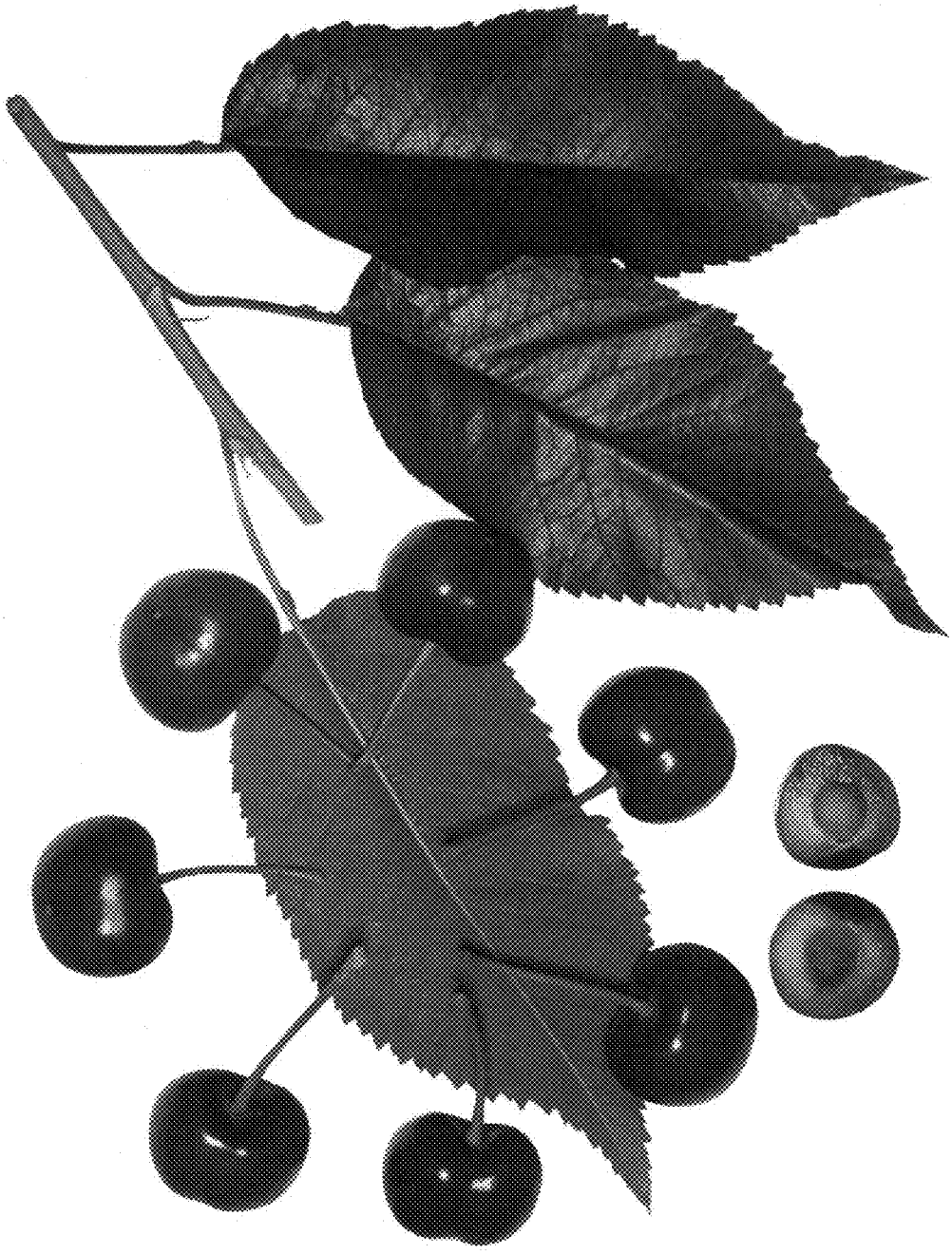

* * * * *